(12) United States Patent
Inagaki

(10) Patent No.: US 10,092,223 B2
(45) Date of Patent: Oct. 9, 2018

(54) MEASUREMENT SYSTEM

(71) Applicant: KYOCERA CORPORATION, Kyoto (JP)

(72) Inventor: Tomohiro Inagaki, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 240 days.

(21) Appl. No.: 14/899,796

(22) PCT Filed: Jun. 24, 2014

(86) PCT No.: PCT/JP2014/003390
§ 371 (c)(1),
(2) Date: Dec. 18, 2015

(87) PCT Pub. No.: WO2014/208084
PCT Pub. Date: Dec. 31, 2014

(65) Prior Publication Data
US 2016/0143563 A1 May 26, 2016

(30) Foreign Application Priority Data
Jun. 27, 2013 (JP) ................................. 2013-135149

(51) Int. Cl.
A61B 5/12 (2006.01)
A61B 5/00 (2006.01)
(Continued)

(52) U.S. Cl.
CPC ............. *A61B 5/121* (2013.01); *H04R 25/30* (2013.01); *H04R 25/407* (2013.01); *H04R 2460/13* (2013.01)

(58) Field of Classification Search
CPC .... A61B 5/121; H04R 25/30; H04R 2460/13; H04R 25/407
(Continued)

(56) References Cited

U.S. PATENT DOCUMENTS 4,251,686 A * 2/1981 Sokolich .................. A61B 5/12
381/338
4,586,194 A * 4/1986 Kohashi ............... H04R 29/001
381/60
(Continued)

FOREIGN PATENT DOCUMENTS

JP S58-198338 A 11/1983
JP H11-500284 A 1/1999
(Continued)

OTHER PUBLICATIONS

English Machine tranaltion for documents KR 100643311 and JP2004179965.*
(Continued)

*Primary Examiner* — Daniel S Larkin
*Assistant Examiner* — Anthony W Megna Fuentes
(74) *Attorney, Agent, or Firm* — Studebaker & Brackett PC

(57) ABSTRACT

This measurement system quantitatively presents the effect of wearing an acoustic device that transmits sound to a user by contacting a vibrating body to a human auricle. In a measurement system including an ear model, which is provided with an artificial auricle and an artificial external ear canal, and an air-conducted sound gauge that measures air-conducted sound in the artificial external ear canal, while an acoustic device is contacted to the ear model of the measurement system, the acoustic device including a vibrating body and transmitting sound to a user by contacting the vibrating body to a human auricle, the measurement system measures, with the air-conducted sound gauge, air-conducted sound generated by the acoustic device and presents the result of measurement together with a characteristic corresponding to when the user wears the acoustic device.

10 Claims, 12 Drawing Sheets

(51) Int. Cl.
  *H04R 25/00* (2006.01)
  *H04R 11/04* (2006.01)
  *H04R 1/10* (2006.01)
(58) Field of Classification Search
  USPC .......................................................... 73/585
  See application file for complete search history.

(56) References Cited

U.S. PATENT DOCUMENTS

| 5,624,377 A | 4/1997 | Davis |
| 2006/0126855 A1* | 6/2006 | Geiger .................. H04R 5/027 381/56 |

FOREIGN PATENT DOCUMENTS

| JP | 2004-179965 A | 6/2004 |
| JP | 2005-348193 A | 12/2005 |
| KR | 10-0643311 B1 | 10/2006 |

OTHER PUBLICATIONS

International Search Report—PCT/JP2014/003390 dated Sep. 30, 2014.
Written Opinion—PCT/JP2014/003390 dated Sep. 30, 2014.
The extended European search report issued by the European Patent Office dated Apr. 11, 2017, which corresponds to European Patent Application No. 14816831.3-1901 and is related to U.S. Appl. No. 14/899,796; 10pp.
Schröter, J. et al.; "On Basic Research Towards an Improved Artificial Head for the Measurement of Hearing Protectors"; Acustica, S. Hirzel Verlag; Stuttgart, Germany; vol. 50; No. 4; Apr. 1, 1982; pp. 250-260.

* cited by examiner

FIG. 3
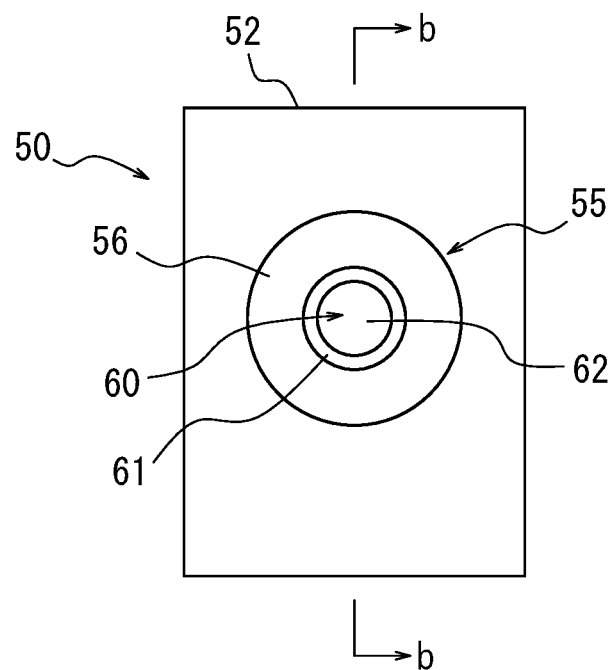
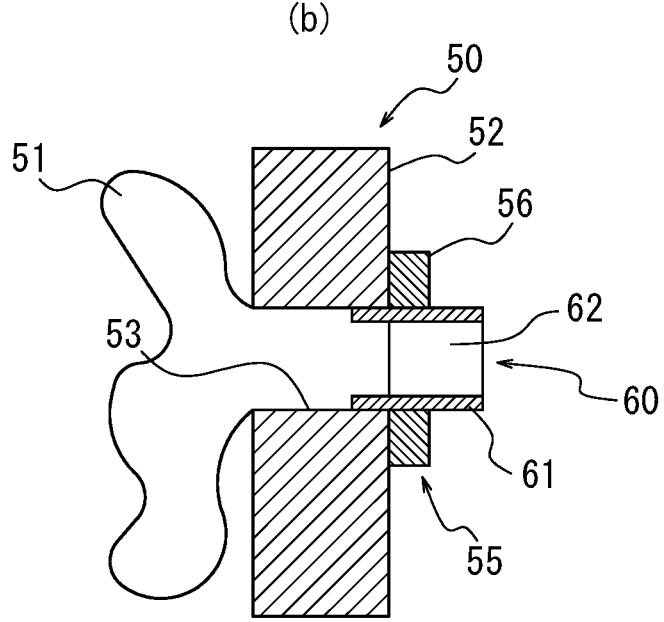

FIG. 5
(a)
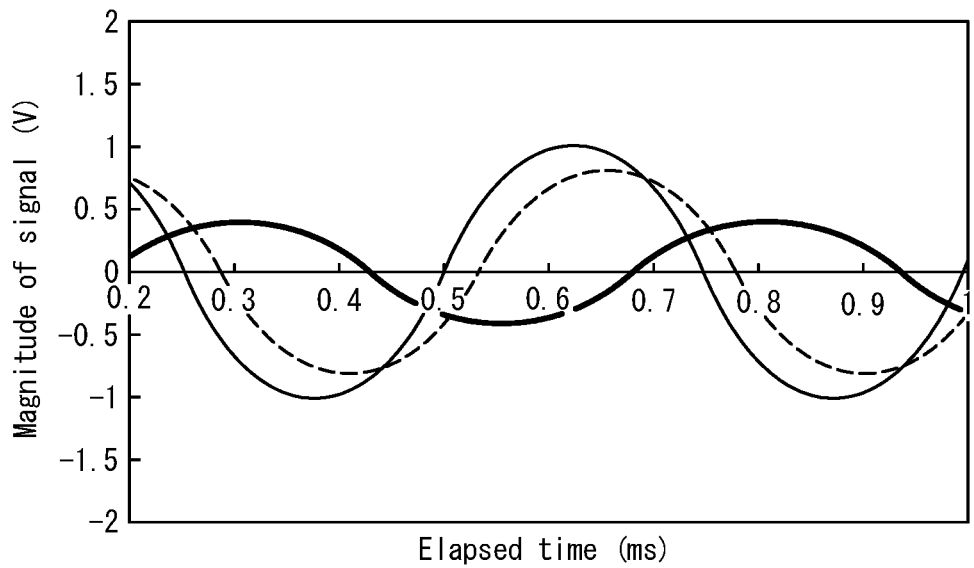
(b)
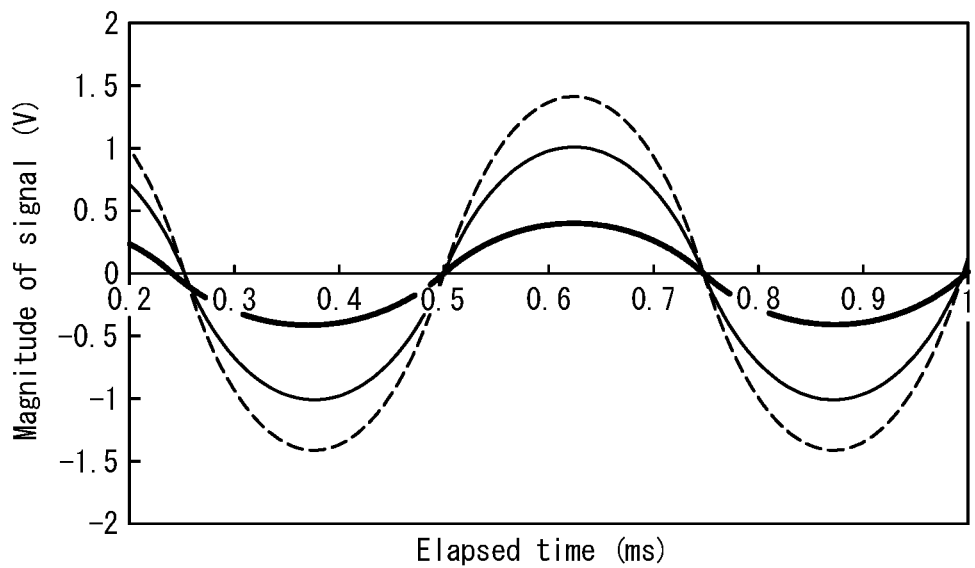

FIG. 7

| Frequency (Hz) | 250 | 500 | 1k | 2k | 4k | 8k |
|---|---|---|---|---|---|---|
| AIR (dB) | 50 | 50 | 50 | 50 | 50 | 50 |
| BONE (dB) | 10 | 10 | 10 | 10 | 10 | 10 |

MEASUREMENT SYSTEM

CROSS-REFERENCE TO RELATED APPLICATION

This application claims priority to and the benefit of Japanese Patent Application No. 2013-135149 filed Jun. 27, 2013, the entire contents of which are incorporated herein by reference.

TECHNICAL FIELD

This disclosure relates to a measurement system for measuring an acoustic device, such as a hearing aid.

BACKGROUND

JP 2005-348193 A (PTL 1) discloses an electronic device, such as a mobile phone or the like, that transmits air-conducted sound and bone-conducted sound to a user. As the air-conducted sound, PTL 1 discloses a sound that is transmitted to the user's auditory nerve by air vibrations, caused by a vibrating object, that are transmitted through the external ear canal to the eardrum and cause the eardrum to vibrate. As the bone-conducted sound, PTL 1 discloses a sound that is transmitted to the user's auditory nerve through a portion of the user's body (such as the cartilage of the outer ear) that is contacting a vibrating object.

In the telephone disclosed in PTL 1, a rectangular plate-shaped vibrating body, formed from a piezoelectric bimorph and a flexible substance, is attached to an outer surface of a housing via an elastic member. PTL 1 also discloses that when voltage is applied to the piezoelectric bimorph in the vibrating body, the piezoelectric material expands and contracts in the longitudinal direction, causing the vibrating body to vibrate. Air-conducted sound and bone-conducted sound are transmitted to the user when the user contacts the vibrating body to the auricle.

CITATION LIST

Patent Literature

PTL 1: JP 2005-348193 A

SUMMARY

Technical Problem

I have developed an acoustic device, such as a hearing aid, that differs from the telephone disclosed in PTL 1 by transmitting sound using air-conducted sound generated by having a vibrating body vibrate a panel disposed in the acoustic device and vibration sound (bone-conducted sound) that is a sound component due to vibration conduction occurring when the vibrating panel is contacted to a human auricle.

A method of measuring volume and a method of adjusting sound quality, however, have not been sufficiently established for acoustic devices such as bone-conduction hearing aids that transmit sound to a user by contacting a vibrating body to a human auricle. In general, the characteristics of an acoustic device such as a bone-conduction hearing aid are displayed as the magnitude of a force generated in a bone-conduction vibrating element (vibrating body), which is pressed against a mechanical coupler (artificial mastoid), when a certain input sound pressure is applied. Therefore, the air-conducted radiation component occurring in the external ear canal of the ear due to vibration and the vibration component transmitted via cartilage of the ear cannot be measured. Moreover, there is no way to present a measured value into which such components are added and simultaneously present characteristics of the effect of wearing the acoustic device.

Therefore, it could be helpful to provide a measurement system that quantitatively presents the effect of wearing an acoustic device that transmits sound to a user by contacting a vibrating body to a human auricle.

Solution to Problem

In order to solve the above problem, the disclosed measurement system includes:
- an ear model including an artificial auricle and an artificial external ear canal; and
- an air-conducted sound gauge configured to measure air-conducted sound in the artificial external ear canal, such that
- while an acoustic device is contacted to the ear model of the measurement system, the acoustic device including a vibrating body and transmitting sound to a user by contacting the vibrating body to a human auricle, the measurement system takes a measurement, with the air-conducted sound gauge, of air-conducted sound generated by the acoustic device and presents a result of the measurement together with a characteristic corresponding to when the user wears the acoustic device.

Advantageous Effect

According to the disclosed measurement system, the effect of wearing an acoustic device that transmits sound to a user by contacting a vibrating body to a human auricle can be presented quantitatively.

BRIEF DESCRIPTION OF THE DRAWINGS

In the accompanying drawings:

FIGS. 3A and 3B are detailed diagrams of the ear model in FIG. 1;

FIGS. 5A and 5B illustrate the phase relationship between output of the vibration detection element and output of the microphone in FIG. 4;

FIG. 7 illustrates hearing test data pertaining to the characteristics in the measurement result screen of FIG. 6;

DETAILED DESCRIPTION

The following describes embodiments with reference to the drawings.

Embodiment 1

Figure 1:
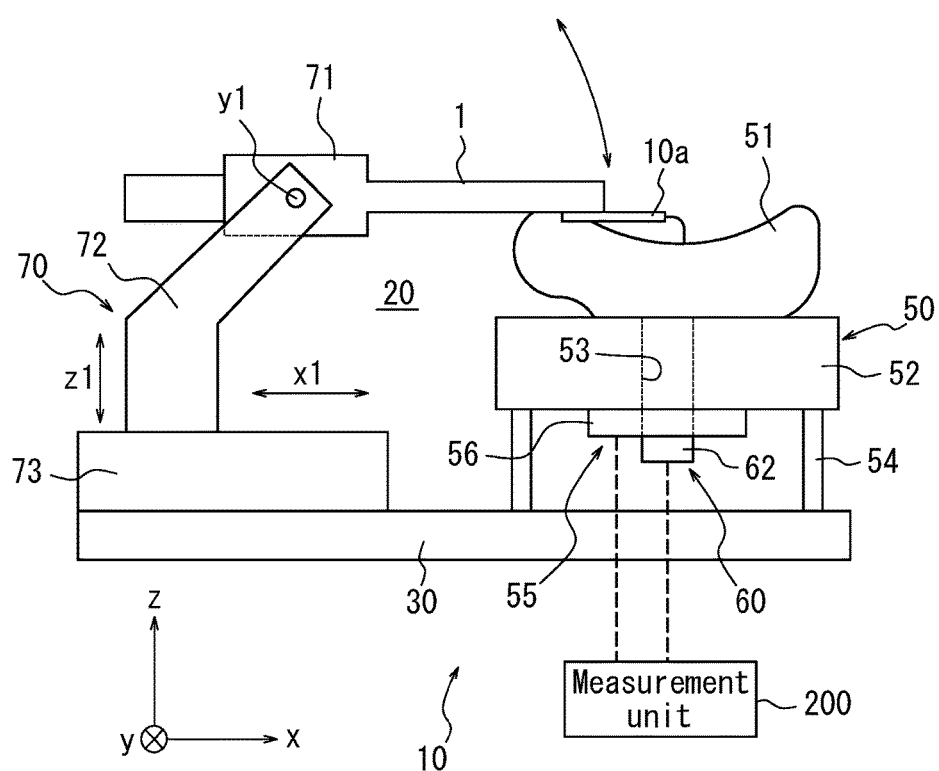
FIG. 1 schematically illustrates the structure of a measurement system according to Embodiment 1.

FIG. 1 schematically illustrates the structure of a measurement system 10 according to Embodiment 1. The measurement system 10 of this embodiment includes an acoustic device mount 20 and a measurement unit 200. The acoustic device mount 20 is provided with an ear model 50 supported by a base 30 and with a holder 70 that supports an acoustic device 1 targeted for measurement. The acoustic device 1 includes a vibrating body and transmits sound to a user by contacting the vibrating body to a human auricle. The acoustic device 1 is, for example, a hearing aid or is a mobile phone, such as a smartphone, that includes a rectangular panel larger than a human ear on a surface of a rectangular housing, with the panel vibrating as a vibrating body.

Figure 2:
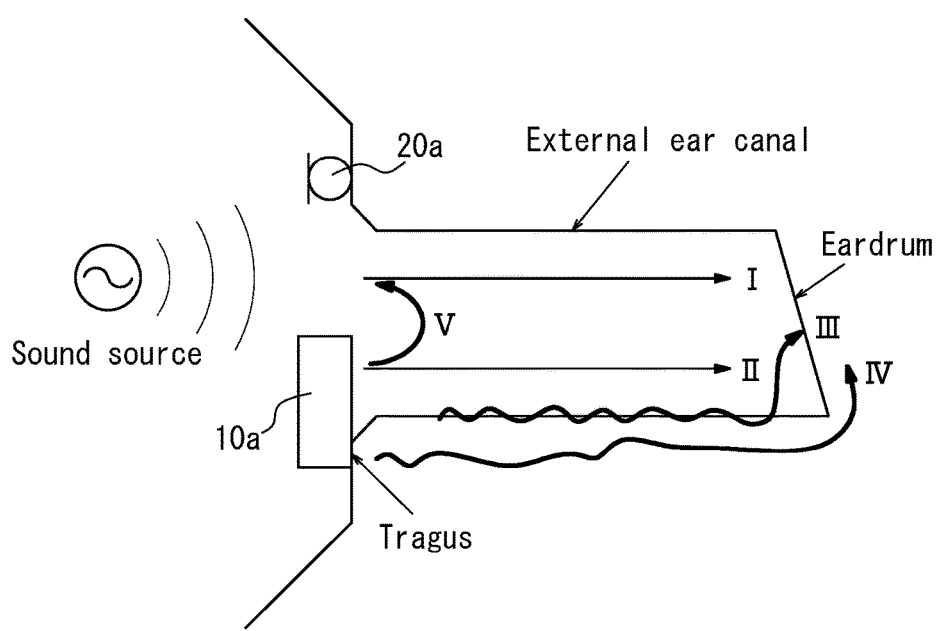
FIG. 2 schematically illustrates an acoustic device according to Embodiment 1.

FIG. 2 schematically illustrates the disclosed acoustic device 1 and the transmission of sound. FIG. 2 illustrates an example of the acoustic device 1 being a hearing aid 1. When the acoustic device 1 is the hearing aid 1, the acoustic device 1 includes a microphone 20a in addition to the vibrating body 10a. The microphone 20a collects sound from a sound source. The vibrating body 10a amplifies the sound collected by the microphone 20a and transmits the sound to the user by vibration.

As illustrated in FIG. 2, sound from the sound source passes through the external ear canal from a portion not covered by the vibrating body 10a and reaches the eardrum directly (path I). Air-conducted sound due to vibration of the vibrating body 10a also passes through the external ear canal and reaches the eardrum (path II). Due to the vibration of the vibrating body 10a, at least the inner wall of the external ear canal vibrates, and air-conducted sound due to this vibration of the external ear canal (external ear canal radiated sound) reaches the eardrum (path III). Furthermore, vibration sound due to the vibration of the vibrating body 10a reaches the auditory nerve directly without passing through the eardrum (path IV). A portion of the air-conducted sound produced by the vibrating body 10a escapes to the outside (path V).

Next, the structure of the acoustic device mount 20 on which the acoustic device 1 is mounted is described. The ear model 50 is modeled after a human ear and includes an artificial auricle 51 and an artificial external ear canal unit 52 joined to the artificial auricle 51. The artificial external ear canal unit 52 is large enough to cover the artificial auricle 51 and has an artificial external ear canal 53 formed in the central region thereof. The ear model 50 is supported by the base 30 via a support member 54 at the periphery of the artificial external ear canal unit 52.

The ear model 50 is made from similar material to the material of an average artificial auricle used in, for example, a manikin such as a Head And Torso Simulator (HATS), Knowles Electronic Manikin for Acoustic Research (KEMAR), or the like, such as material conforming to IEC 60318-7. This material may, for example, be formed with a material such as rubber having a hardness of 35 to 55. The hardness of rubber may, for example, be measured in conformity with International Rubber Hardness Degrees (IRHD/M) conforming to JIS K 6253, ISO 48, or the like. As a hardness measurement system, a fully automatic IRHD/M micro-size international rubber hardness gauge GS680 by Teclock Corporation may suitably be used. Note that considering the variation in ear hardness due to age, as a rule of thumb, approximately two or three types of the ear model 50 with a different hardness are preferably prepared and used interchangeably.

The thickness of the artificial external ear canal unit 52, i.e. the length of the artificial external ear canal 53, corresponds to the length up to the human eardrum (cochlea) and for example is suitably set in a range of 20 mm to 40 mm. In this embodiment, the length of the artificial external ear canal 53 is approximately 30 mm.

In the ear model 50, a vibration sound gauge 55 is disposed on the end face of the artificial external ear canal unit 52 on the opposite side from the artificial auricle 51, at a position in the peripheral portion of the opening of the artificial external ear canal 53. The vibration sound gauge 55 detects the amount of vibration transmitted through the artificial external ear canal unit 52 when the vibrating body of the acoustic device 1 is placed against the ear model 50. In other words, the vibration sound gauge 55 detects the amount of vibration corresponding to the vibration sound component that is heard without passing through the eardrum when the vibrating body of the acoustic device 1 is pressed against a human ear and vibration of the vibrating body of the acoustic device 1 directly vibrates the inner ear. As used here, vibration sound refers to sound that is transmitted to the user's auditory nerve through a portion of the user's body (such as the cartilage of the outer ear) that is contacting a vibrating object. The vibration sound gauge 55 is, for example, configured using a vibration detection element 56 that has flat output characteristics in the measurement frequency range of the acoustic device 1 (for example, from 0.1 kHz to 30 kHz), is lightweight, and can accurately measure even slight vibrations. An example of this vibration detection element 56 is a piezoelectric acceleration pickup or other such vibration pickup, such as the vibration pickup PV-08A produced by Rion Corporation or the like.

FIG. 3A is a plan view of the ear model 50 from the base 30 side. While FIG. 3A illustrates an example of providing a ring-shaped vibration detection element 56 that surrounds the peripheral portion of the opening of the artificial external ear canal 53, a plurality of vibration detection elements 56 may be provided instead of only one. In the case of providing a plurality of vibration detection elements 56, the vibration detection elements 56 may be disposed at appropriate intervals at the periphery of the artificial external ear canal 53, or two arc-shaped vibration detection elements 56 may be disposed to surround the periphery of the opening in the artificial external ear canal 53. In FIG. 3A, the artificial external ear canal unit 52 is rectangular, yet the artificial external ear canal unit 52 may be any shape.

Furthermore, an air-conducted sound gauge 60 is disposed in the ear model 50. The air-conducted sound gauge 60 measures the sound pressure of sound propagating through the artificial external ear canal 53. In other words, the air-conducted sound gauge 60 measures the sound pressure produced when the vibrating body of the acoustic device 1 is pressed against a human ear. This sound pressure includes sound pressure corresponding to air-conducted sound that is heard directly through the eardrum by air vibrating due to vibration of the vibrating body of the acoustic device 1 and sound pressure corresponding to air-conducted sound representing sound, heard through the eardrum, that is produced in the ear itself by the inside of the external ear canal vibrating due to vibration of the vibrating body of the acoustic device 1. Air-conducted sound is sound transmitted to the user's auditory nerve by air vibrations, caused by a vibrating object, that are transmitted through the external ear canal to the eardrum and cause the eardrum to vibrate. Furthermore, when a different sound source from the acoustic device 1 exists, the air-conducted sound gauge 60 also measures sound pressure of direct sound from this sound source.

As illustrated by the cross-sectional view in FIG. 3B along the b-b line in FIG. 3A, the air-conducted sound gauge 60 includes a microphone 62 held by a tube member 61 that extends from the outer wall (peripheral wall of the hole) of the artificial external ear canal 53 through the opening of the ring-shaped vibration detection element 56. The microphone 62 is, for example, configured using a measurement capacitor microphone that has a low self-noise level and that has flat output characteristics in the measurement frequency range of the acoustic device 1. The capacitor microphone UC-53A produced by Rion Corporation may, for example, be used as the microphone 62. The microphone 62 is disposed so that the sound pressure detection face nearly matches the end face of the artificial external ear canal unit 52. The microphone 62 may, for example, be supported by the artificial external ear canal unit 52 or the base 30 and disposed in a floating state with respect to the outer wall of the artificial external ear canal 53.

Next, the holder 70 is described. The holder 70 is provided with a support 71 that supports the acoustic device 1. The support 71 is attached to one end of an arm 72 so as to be rotatable about an axis y1, which is parallel to the y-axis, in a direction to press the acoustic device 1 (only the panel 10a of the acoustic device 1 being illustrated schematically in FIG. 1) against the ear model 50. The other end of the arm 72 is joined to a movement adjuster 73 provided on the base 30. The movement adjuster 73 can adjust movement of the arm 72 in a vertical direction x1 (i.e., vertical with respect to the ear model 50) of the acoustic device 1 supported by the support 71, the direction x1 being parallel to the x-axis that is orthogonal to the y-axis, and in a direction z1 that presses the acoustic device 1 against the ear model 50, the direction z1 being parallel to the z-axis that is orthogonal to the y-axis and the x-axis.

In this way, in the acoustic device 1 supported by the support 71, the pressing force, against the ear model 50, of the vibrating body is adjusted by rotating the support 71 about the axis y1 or by moving the arm 72 in the z1 direction. In this embodiment, the pressing force is adjusted in a range of 0 N to 10 N. Of course, the support 71 may also be configured to rotate freely about other axes in addition to the y1 axis.

The case of 0 N may, for example, include not only the case of contacting without pressing against the ear model 50, but also the case of holding the acoustic device 1 at a distance from the ear model 50 in increments of 1 cm and measuring at each distance. This approach also allows measurement with the microphone 62 of the degree of damping of air-conducted sound due to distance, thus making the measurement system more convenient.

By adjusting the arm 72 in the x1 direction, the contact position of the acoustic device 1 with respect to the ear model 50 can be adjusted so that, for example, the vibrating body covers nearly the entire ear model 50, or so that the vibrating body covers a portion of the ear model 50, as illustrated in FIG. 1. A configuration may also be adopted to allow adjustment of the acoustic device 1 to a variety of contact positions with respect to the ear model 50 by making movement of the arm 72 adjustable in a direction parallel to the y-axis, or by making the arm 72 rotatable about an axis parallel to the x-axis or the z-axis. The vibrating body is not limited to an object like a panel that widely covers the ear, and for example an acoustic device having a protrusion or corner that transmits vibration to only a portion of the ear model 50, such as the tragus, may be targeted for measurement.

Figure 4:
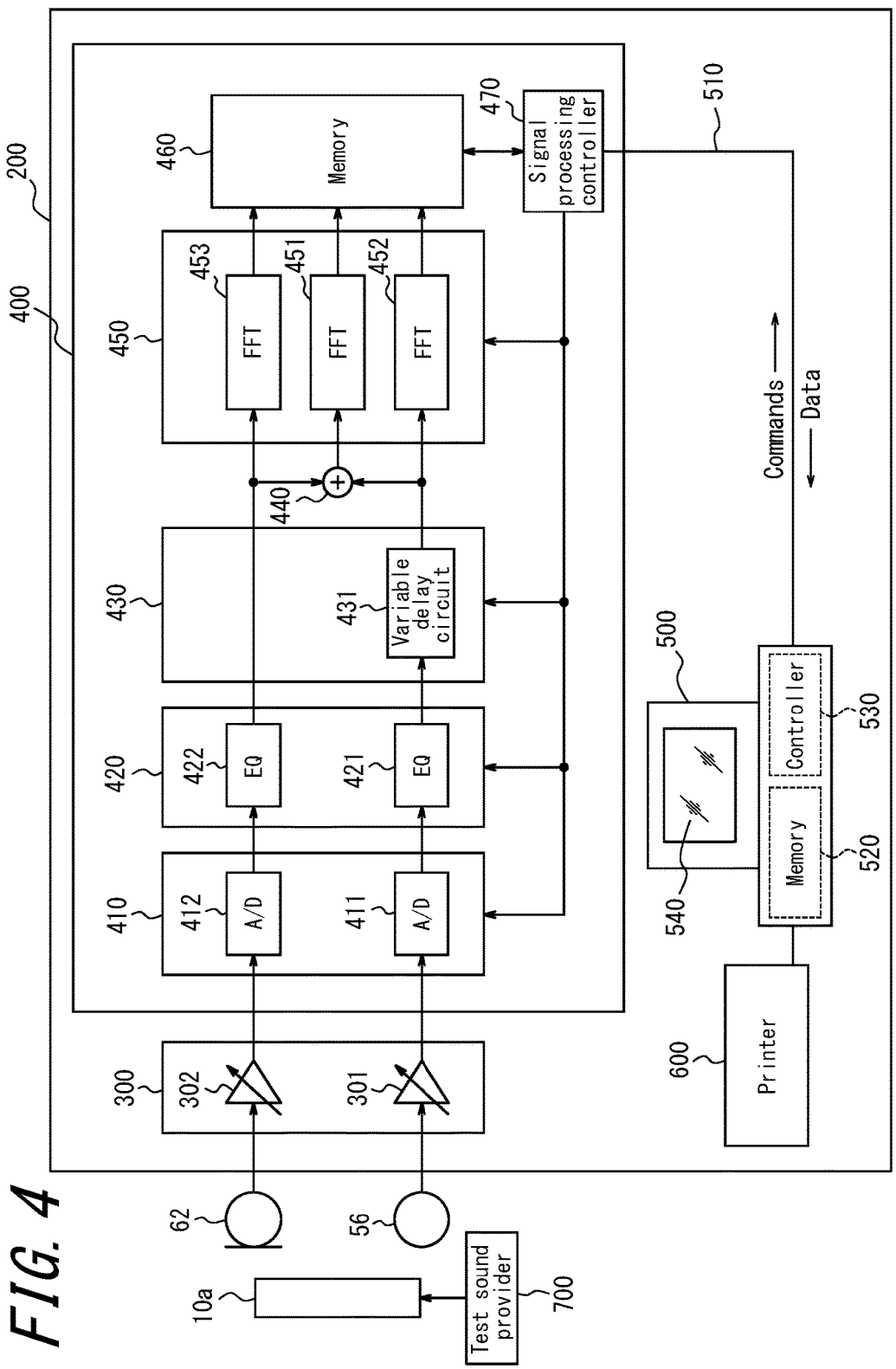
FIG. 4 is a functional block diagram illustrating the structure of a section of the measurement unit in FIG. 1.

Next, the structure of the measurement unit 200 in FIG. 1 is described. FIG. 4 is a functional block diagram illustrating the structure of a section of the measurement unit 200. In this embodiment, the measurement unit 200 measures the amount of vibration and the sound pressure transmitted through the ear model 50 by vibration of the acoustic device 1 targeted for measurement, i.e. sensory sound pressure that combines vibration sound and air-conducted sound, and includes a sensitivity adjuster 300, signal processor 400, personal computer (PC) 500, printer 600, and test sound provider 700.

Output of the vibration detection element 56 and the microphone 62 is provided to the sensitivity adjuster 300. The sensitivity adjuster 300 includes a variable gain amplifier circuit 301 that adjusts the amplitude of the output of the vibration detection element 56 and a variable gain amplifier circuit 302 that adjusts the amplitude of the output of the microphone 62. The amplitudes of analog input signals, corresponding to the respective circuits, are independently adjusted to required amplitudes either manually or automatically. Error in the sensitivity of the vibration detection element 56 and the sensitivity of the microphone 62 is thus corrected. Note that the variable gain amplifier circuits 301 and 302 are configured to allow adjustment of the amplitude of the input signals over a range of, for example, ±50 dB.

Output of the sensitivity adjuster 300 is input into the signal processor 400. The signal processor 400 includes an A/D converter 410, frequency characteristic adjuster 420, phase adjuster 430, output combiner 440, frequency analyzer 450, memory 460, and signal processing controller 470. The A/D converter 410 includes an A/D conversion circuit (A/D) 411 that converts the output of the variable gain amplifier circuit 301 into a digital signal and an A/D conversion circuit (A/D) 412 that converts the output of the variable gain amplifier circuit 302 into a digital signal. The analog input signal corresponding to each circuit is thus converted into a digital signal. The A/D conversion circuits 411 and 412 are, for example, 16 bits or more and can support 96 dB or more by dynamic range conversion. The A/D conversion circuits 411 and 412 may also be configured so that the dynamic range is changeable.

Output of the A/D converter 410 is provided to the frequency characteristic adjuster 420. The frequency characteristic adjuster 420 includes an equalizer (EQ) 421 that adjusts the frequency characteristics of the detection signal from the vibration detection element 56, i.e. the output of the A/D conversion circuit 411, and an equalizer (EQ) 422 that adjusts the frequency characteristics of the detection signal from the microphone 62, i.e. the output of the A/D conversion circuit 412. The frequency characteristics of the respective input signals are independently adjusted to frequency characteristics near the auditory sensation of the human body either manually or automatically. The equalizers 421 and 422 may, for example, be configured with a graphical equalizer having a plurality of bands, a low pass filter, a high pass filter, or the like. The order in which the equalizers (EQ) and the A/D conversion circuits are disposed may be reversed.

Output of the frequency characteristic adjuster 420 is provided to the phase adjuster 430. The phase adjuster 430 includes a variable delay circuit 431 that adjusts the phase of the detection signal from the vibration detection element 56, i.e. the output of the equalizer 421. In other words, since the speed of sound transmitted through the material of the ear model 50 is not exactly the same as the speed of sound transmitted through human muscle or bone, it is assumed that the phase relationship between the output of the vibration detection element 56 and the output of the microphone 62 will be shifted from that of a human ear, the shift being greater at high frequencies.

If the phase relationship between the output of the vibration detection element 56 and the output of the microphone 62 thus shifts greatly, then upon combining the two outputs with the below-described output combiner 440, amplitude peaks and dips may appear at different values than in actuality, and the combined output may be amplified or diminished. For example, if the transmission speed of sound detected by the microphone 62 is 0.2 ms slower than the transmission speed of vibration detected by the vibration detection element 56, then the combined output of both as sinusoidal vibration at 2 kHz is as illustrated in FIG. 5A. By contrast, the combined output when there is no misalignment in the transmission speeds is as illustrated in FIG. 5B, and amplitude peaks and dips appear at unnatural times. In FIGS. 5A and 5B, the bold line indicates a vibration waveform detected by the vibration detection element 56, the thin line indicates a sound pressure waveform detected by the microphone 62, and the dashed line indicates the waveform of the combined output.

Therefore, in this embodiment, in accordance with the measurement frequency range of the acoustic device 1 targeted for measurement, the phase of the detection signal from the vibration detection element 56, which is the output of the equalizer 421, is adjusted over a predetermined range by the variable delay circuit 431. For example, in the case of the measurement frequency range of the acoustic device 1 being from 100 Hz to 10 kHz, the phase of the detection signal from the vibration detection element 56 is adjusted by the variable delay circuit 431 over a range of approximately ±10 ms (corresponding to ±100 Hz) at least in increments smaller than 0.1 ms (corresponding to 10 kHz). In the case of a human ear as well, phase misalignment occurs between vibration sound and air-conducted sound. Therefore, phase adjustment by the variable delay circuit 431 does not refer to matching the phase of the detection signals from the vibration detection element 56 and the microphone 62, but rather to matching the phase of these detection signals to the actual auditory sensation by the ear.

Output of the phase adjuster 430 is provided to the output combiner 440. The output combiner 440 combines the detection signal from the vibration detection element 56, after phase adjustment by the variable delay circuit 431, with the detection signal, from the microphone 62, that has passed through the phase adjuster 430. This allows approximation of the human body in obtaining sensory sound pressure that combines the amount of vibration and the sound pressure, i.e. the vibration sound and the air-conducted sound, transmitted by vibration of the acoustic device 1 targeted for measurement.

The combined output of the output combiner 440 is input into the frequency analyzer 450. The frequency analyzer 450 includes a Fast Fourier Transform (FFT) 451 that performs frequency analysis on the combined output of the output combiner 440. In this way, power spectrum data corresponding to combined sound, i.e. the sensory sound pressure (air+vib) in which the vibration sound (vib) and the air-conducted sound (air) are combined, are obtained from the FFT 451.

Furthermore, in this embodiment, the frequency analyzer 450 is provided with FFTs 452 and 453 that perform frequency analysis on the signals before combination by the output combiner 440, i.e. on the detection signal, from the vibration detection element 56, that has passed through the phase adjuster 430 and the detection signal from the microphone 62. In this way, power spectrum data corresponding to the vibration sound (vib) are obtained from the FFT 452, and power spectrum data corresponding to the air-conducted sound (air) are obtained from the FFT 453.

In the FFTs 451 to 453, analysis points are set for the frequency component (power spectrum) in correspondence with the measurement frequency range of the acoustic device 1. For example, when the measurement frequency range of the acoustic device 1 is 100 Hz to 10 kHz, analysis points are set so as to analyze the frequency component at each point when dividing the interval in a logarithmic graph of the measurement frequency range into 100 to 2000 equal portions.

The output of the FFTs 451 to 453 is stored in the memory 460. The memory 460 has the capacity of at least a double buffer that can store a plurality of analysis data sets (power spectrum data) for each of the FFTs 451 to 453. The memory 460 is configured to always allow transmission of the latest data upon a data transmission request from the below-described PC 500.

The signal processing controller 470 is connected to the PC 500 via a connection cable 510 for an interface such as USB, RS-232C, SCSI, PC card, or the like. Based on commands from the PC 500, the signal processing controller 470 controls operations of each portion of the signal processor 400. The signal processor 400 may be configured as software executed on any suitable processor, such as a Central Processing Unit (CPU), or may be configured with a Digital Signal Processor (DSP).

The PC 500 includes an evaluation application that, using the measurement system 10, presents the effect of wearing the acoustic device 1. The evaluation application is, for example, copied from a CD-ROM or downloaded over a network or the like and is stored in a memory 520. The PC 500 executes the evaluation application with a controller 530. The PC 500 for example displays an application screen on a display 540 based on the evaluation application. Based on information input via the application screen, the PC 500 transmits a command to the signal processor 400. The PC 500 also receives a command acknowledgment and data from the signal processor 400, and based on the received data, executes predetermined processing and displays the measurement results on the application screen. As necessary, the PC 500 also outputs the measurement results to the printer 600 to print the measurement results.

In FIG. 4, the sensitivity adjuster 300 and the signal processor 400 may, for example, be mounted on the base 30 of the acoustic device mount 20, with the PC 500 and printer 600 being disposed separately from the base 30, and the signal processor 400 and PC 500 being connected by a connection cable 510.

With a non-illustrated test signal generator, the test sound provider 700 can generate a single frequency sine wave signal (pure tone), a pure tone sweep signal, a multi-sine wave, a warble tone, band noise, or the like and present the test sound with a speaker function. Instead of presenting the test sound with a speaker function, the test sound provider 700 may be connected to an external terminal of the acoustic device 1 and input the test sound to the acoustic device 1 as an input signal.

Figure 6:
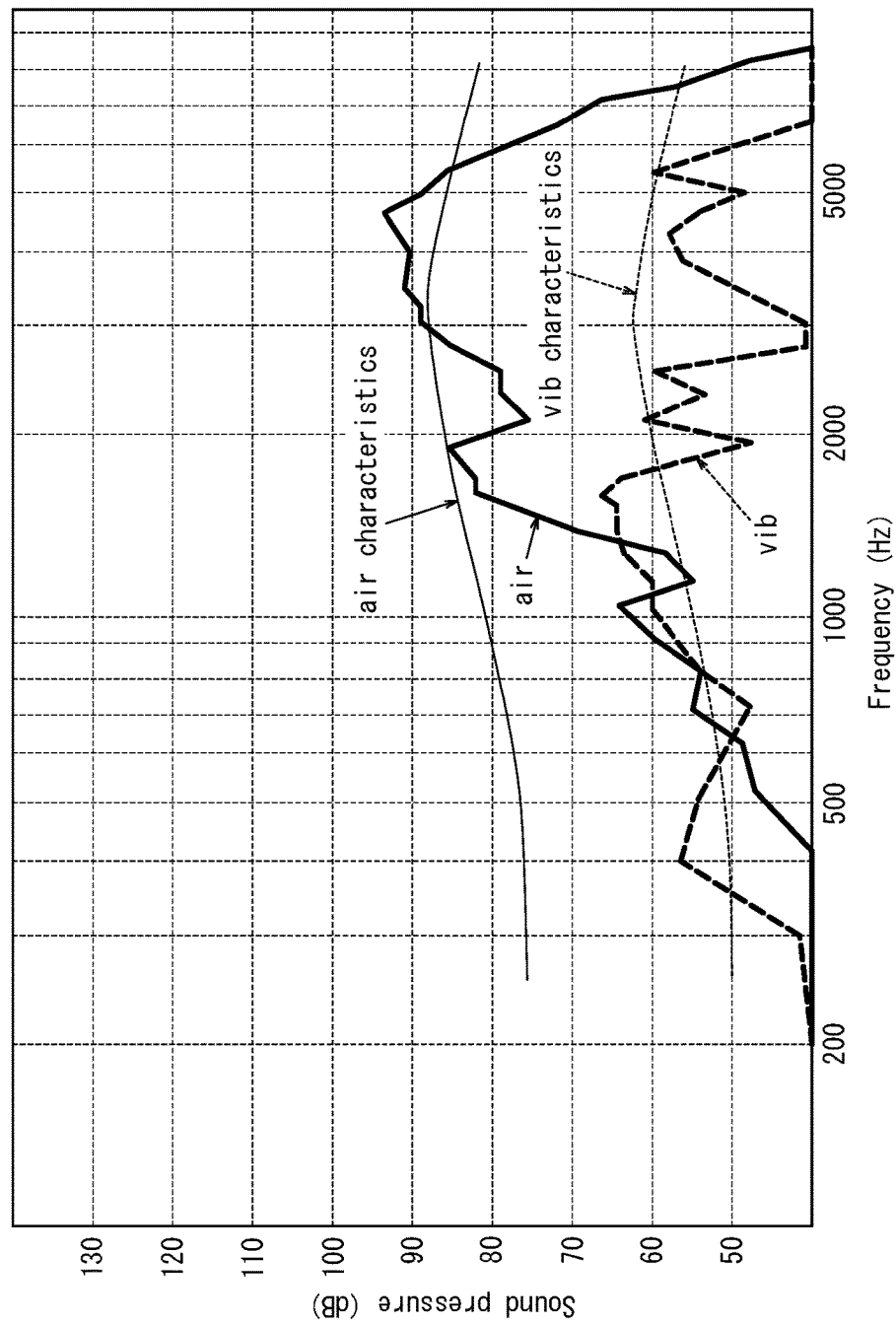
FIG. 6 illustrates an example of a measurement result screen.

FIG. 6 illustrates an example of a measurement result screen displayed on the display 540. The air-conducted sound (air) measured by the air-conducted sound gauge 60 and the vibration sound (vib) measured by the vibration sound gauge 55 are displayed on the measurement result screen. The characteristics pertaining to air-conducted sound ("air characteristics") and characteristics pertaining to vibration sound ("vib characteristics") that are the target when the user wears the acoustic device 1 (target effect of wearing) are also displayed on the measurement result screen. As the air-conducted sound and vibration sound emitted by the acoustic device 1 are respectively closer to the air characteristics and the vib characteristics, the sound that is heard is more pleasant for the user. As the emitted sound falls below these characteristics, the sound heard by the user becomes too quiet and is difficult to hear, but as the sound exceeds these characteristics, the sound heard by the user becomes too loud and is difficult to hear.

The characteristics pertaining to air-conducted sound and the characteristics pertaining to vibration sound may be determined with reference to data obtained in advance by a hearing test, with a predetermined air-conducted sound pressure (for example, 50 dB) set as the target for the user's ear. FIG. 7 illustrates data, corresponding to the characteristics in FIG. 6, obtained by a hearing test. These data are preferably stored in the memory 520 of the PC 500. The "AIR" in FIG. 7 represents data pertaining to air-conducted sound obtained by the hearing test (air-conducted threshold at each frequency for an air-conducted receiver). In this case, the user cannot hear sound that is less than the air-conducted threshold. The "BONE" in FIG. 7 represents data pertaining to vibration sound obtained by the hearing test (bone-conducted threshold at each frequency for a bone-conducted receiver). In this case, the user cannot hear sound that is less than the bone-conducted threshold.

For the "AIR" in FIG. 7, the air-conducted threshold is 50 dB for each of 250 Hz, 500 Hz, 1000 Hz (1 kHz), 2000 Hz (2 kHz), 4000 Hz (4 kHz), and 8000 Hz (8 kHz). In other words, the user cannot hear air-conducted sound unless the sound is at least 50 dB at each frequency. On the other hand, for the data pertaining to vibration sound, the bone-conducted threshold is 10 dB for each of 250 Hz, 500 Hz, 1000 Hz, 2000 Hz, 4000 Hz, and 8000 Hz. In other words, the user can hear vibration sound at a nearly normal volume at each frequency. Accordingly, the hearing test results in FIG. 7 demonstrate that the cause of the user's hearing loss lies between the outer ear and the middle ear. The user thus suffers from conductive hearing loss. A variety of methods have been proposed for calculating characteristics based on the data in FIG. 7 obtained with a hearing test. Among these methods, FIG. 6 illustrates the results of calculation with a method referred to as FIG. 6.

As illustrated in FIG. 6, according to the disclosed measurement system 10, the effect of wearing the acoustic device 1 that transmits sound to a user by contacting a vibrating body to a human auricle can be presented quantitatively. Based on the presented effect of wearing the acoustic device 1, the sound pressure of the air-conducted sound and the vibration sound emitted by the acoustic device 1 can be adjusted comprehensively. This adjustment is, for example, made with a plurality of trimmers disposed in the acoustic device 1. By adjusting the acoustic gain at each frequency with the trimmers to change the sound pressure, the acoustic device 1 can be matched to the user's hearing level. For example, in the example in FIG. 6, adjustments are made in the low frequency range (100 Hz to 1000 Hz) so that the vibration sound approaches the target characteristics (vib characteristics). Adjustments are also made in the high frequency range (2000 Hz to 10000 Hz) so that the air-conducted sound approaches the target characteristics (air characteristics).

The air-conducted sound and vibration sound emitted by the acoustic device 1 are determined based on the structure by which the vibrating body of the acoustic device 1 is pressed against the ear. In greater detail, the ratio between the air-conducted sound and the vibration sound emitted by the acoustic device 1 is determined at each frequency as $\alpha:\beta$ or the like by the structure for pressing against the ear. Therefore, it is impossible to make adjustments that, for example, increase the sound pressure of only the air-conducted sound or only the vibration sound. Therefore, based on the effect of wearing the acoustic device 1 as presented by the disclosed measurement system 10, when the sound pressure is gradually increased from 0, adjustments are made to approach the characteristics of whichever of the vibration sound and the air-conducted sound that the user hears first (air characteristics or vib characteristics). Making adjustments in this way prevents either the air-conducted sound or the vibration sound from becoming louder than necessary and allows adjustments that are comfortable for the user to be made easily.

Figure 8:
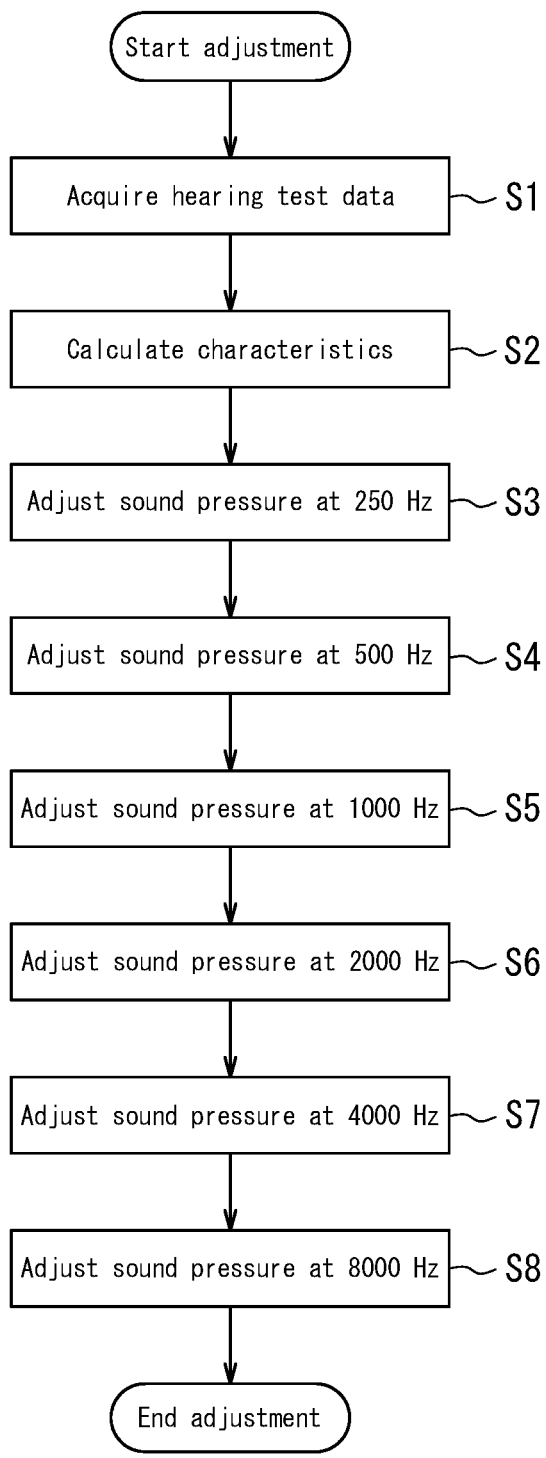
FIG. 8 is a flowchart illustrating an example of adjustment of an acoustic device 1.

FIG. 8 is a flowchart illustrating an example of adjustment of the acoustic device 1 with the disclosed measurement system. Adjustment of the acoustic device 1 is described below as being performed by the controller 530 of the PC 500.

First, the controller 530 of the PC 500 acquires the data obtained by a hearing test from the memory 520 (step S1). In this example, data are acquired at the frequencies of 250 Hz, 500 Hz, 1000 Hz, 2000 Hz, 4000 Hz, and 8000 Hz.

Next, based on the acquired hearing test data, the controller 530 calculates characteristics pertaining to air-conducted sound and vibration sound (step S2). The calculation is, for example, made with FIG. 6.

The controller 530 then makes adjustments by gradually increasing the sound pressure of the acoustic device 1 from 0 at 250 Hz so that the output sound pressure of either the air-conducted sound or vibration sound of the acoustic device 1 at 250 Hz approaches the characteristics pertaining to air-conducted sound or vibration sound (step S3).

The controller 530 then makes adjustments by gradually increasing the sound pressure of the acoustic device 1 from 0 at 500 Hz so that the output sound pressure of either the air-conducted sound or vibration sound of the acoustic device 1 at 500 Hz approaches the characteristics pertaining to air-conducted sound or vibration sound (step S4).

The controller 530 then makes adjustments by gradually increasing the sound pressure of the acoustic device 1 from 0 at 1000 Hz so that the output sound pressure of either the air-conducted sound or vibration sound of the acoustic device 1 at 1000 Hz approaches the characteristics pertaining to air-conducted sound or vibration sound (step S5).

The controller 530 then makes adjustments by gradually increasing the sound pressure of the acoustic device 1 from 0 at 2000 Hz so that the output sound pressure of either the air-conducted sound or vibration sound of the acoustic device 1 at 2000 Hz approaches the characteristics pertaining to air-conducted sound or vibration sound (step S6).

The controller 530 then makes adjustments by gradually increasing the sound pressure of the acoustic device 1 from 0 at 4000 Hz so that the output sound pressure of either the air-conducted sound or vibration sound of the acoustic device 1 at 4000 Hz approaches the characteristics pertaining to air-conducted sound or vibration sound (step S7).

The controller 530 then makes adjustments by gradually increasing the sound pressure of the acoustic device 1 from 0 at 8000 Hz so that the output sound pressure of either the air-conducted sound or vibration sound of the acoustic device 1 at 8000 Hz approaches the characteristics pertaining to air-conducted sound or vibration sound (step S8). The adjustment process then terminates.

Making adjustments in this way prevents either the air-conducted sound or the vibration sound from becoming louder than necessary and allows adjustments that are comfortable for the user to be made easily. While the sound pressure is adjusted at the frequencies of 250 Hz, 500 Hz, 1000 Hz, 2000 Hz, 4000 Hz, and 8000 Hz in the above-described adjustment of the acoustic device 1, adjustment is not limited to these frequencies and may be made at other frequencies. In the above-described example, the controller 530 of the PC 500 adjusts the acoustic device 1, but this example is not limiting. For example, while watching the measurement result screen, an operator may make manual adjustments so that the output sound pressure of either the air-conducted sound or the vibration sound at each frequency of the acoustic device 1 approaches the target characteristics.

Figure 9:
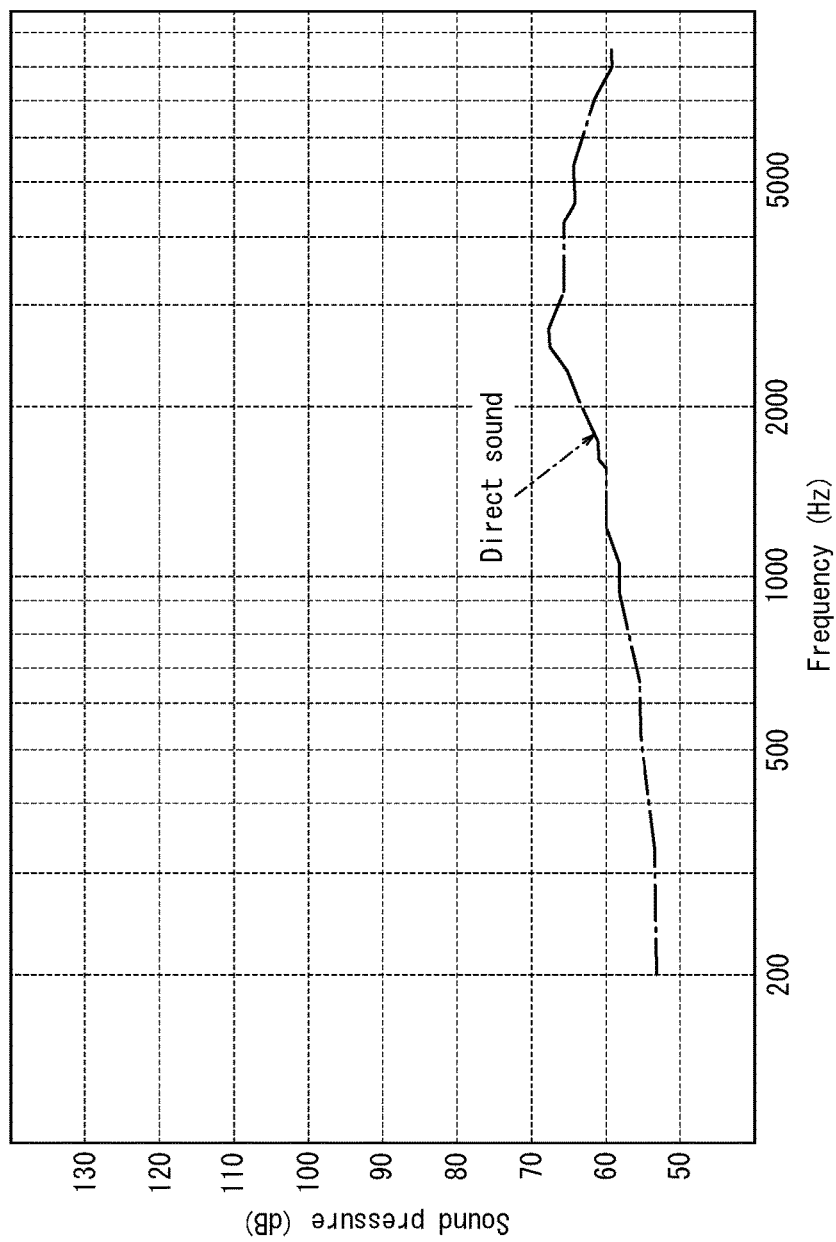
FIG. 9 illustrates the spectrum of direct sound from a sound source.

In the above embodiment, only the air-conducted sound and vibration sound emitted by the acoustic device 1 are taken into consideration, but this example is not limiting. Direct sound from a sound source, i.e. sound over path I in FIG. 2, may be added in. FIG. 9 illustrates power spectrum data of direct sound from a sound source. By also adding in the direct sound from a sound source illustrated in FIG. 9, adjustments to the acoustic device 1 that conform more closely to the actual form of use can be made.

The measurement result screen in FIG. 6 illustrates the data on air-conducted sound, vibration sound, and characteristics as curves on a graph corresponding to the frequency band, but this example is not limiting. For example, these data may be displayed as numerical values corresponding to certain frequencies.

In this embodiment, air-conducted sound, vibration sound, characteristics pertaining to air-conducted sound, and characteristics pertaining to vibration sound are displayed on the measurement result screen, but this example is not limiting. The measurement result screen may be configured to display only air-conducted sound and characteristics pertaining to air-conducted sound. The measurement result screen may also be configured to display only vibration sound and characteristics pertaining to vibration sound. Evaluation software on the PC 500 may also function to switch between such displays so as to display only necessary information, while hiding the display of unnecessary information.

Figure 10:
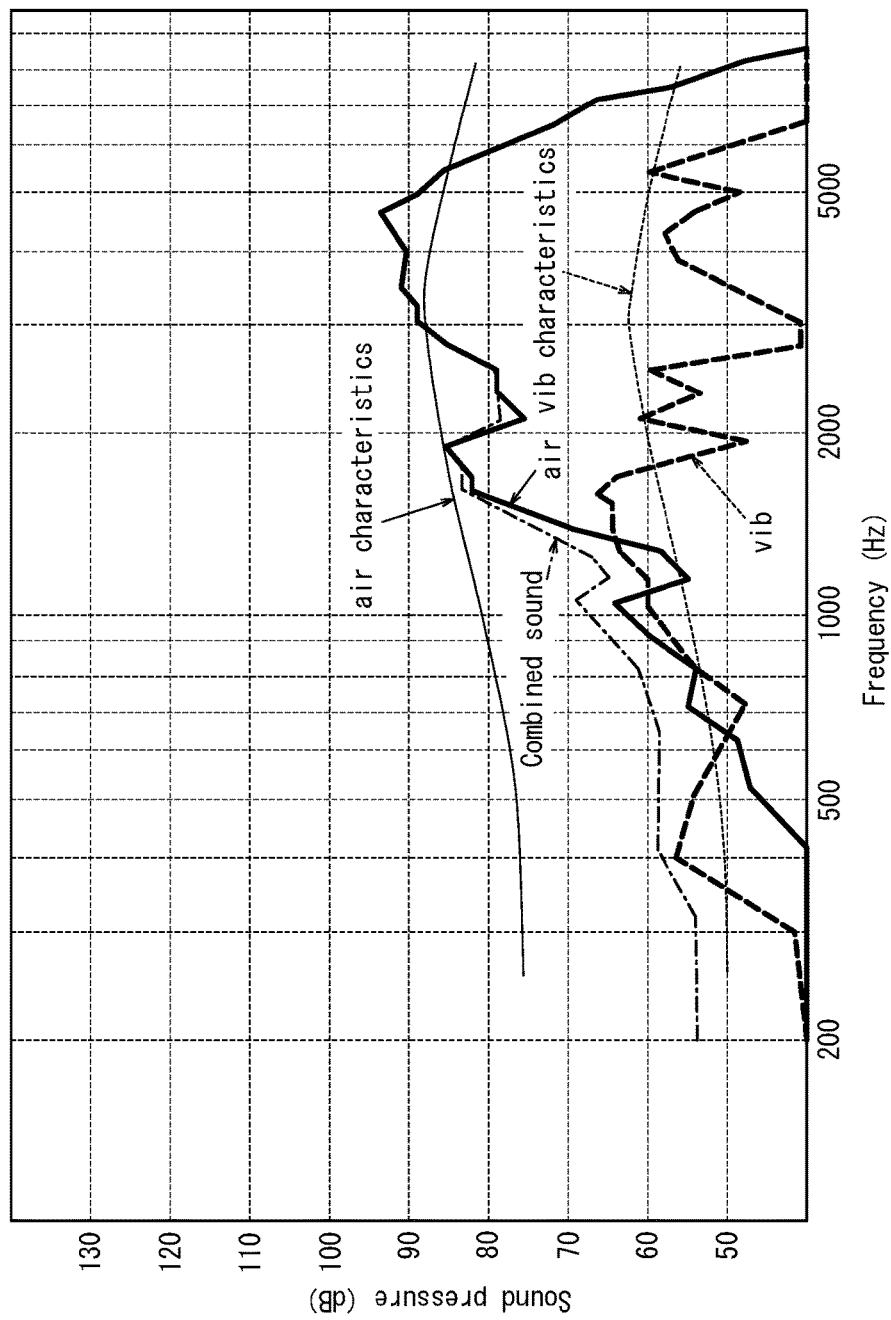
FIG. 10 illustrates an example of a measurement result screen that adds in direct sound from a sound source.

While the air-conducted sound and vibration sound are presented separately in this embodiment, a combined sound may also be presented. FIG. 10 illustrates a measurement result screen for the case of outputting a combined sound that is a combination of air-conducted sound, vibration sound, and direct sound from a sound source. In this case, the combined sound of the air-conducted sound, vibration sound, and direct sound, and the characteristics pertaining to the combined sound of the air-conducted sound and vibration sound, which are the target when the user wears the acoustic device 1, are displayed.

Embodiment 2

The following describes Embodiment 2. As compared to Embodiment 1, the structure of the measurement system 110 differs in Embodiment 2. The remaining structure is the same as in Embodiment 1. Where the structure is the same as in Embodiment 1, the same reference signs are applied, and a description thereof is omitted.

Figure 11:
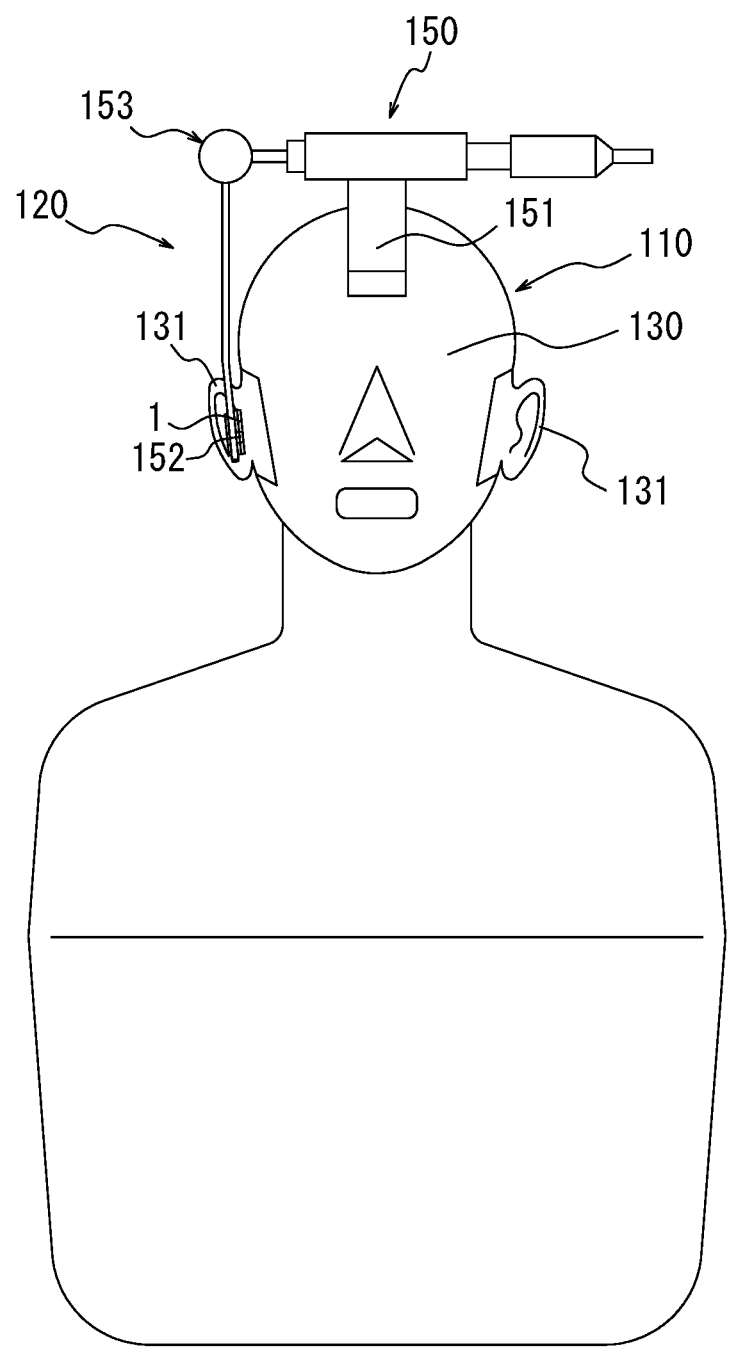
FIG. 11 schematically illustrates the structure of a section of a measurement system according to Embodiment 2.

FIG. 11 schematically illustrates the structure of a section of a measurement system 110 according to Embodiment 2. In the measurement system 110 of this embodiment, the structure of an acoustic device mount 120 differs from that of the acoustic device mount 20 in Embodiment 1, whereas the remaining structure is similar to that of Embodiment 1. Accordingly, the measurement unit 200 in Embodiment 1 is omitted from FIG. 11. The acoustic device mount 120 is provided with a human head model 130 and a holder 150 that holds the acoustic device 1 targeted for measurement. The head model 130 is, for example, HATS, KEMAR, or the like. Artificial ears 131 of the head model 130 are detachable from the head model 130.

Figure 12:
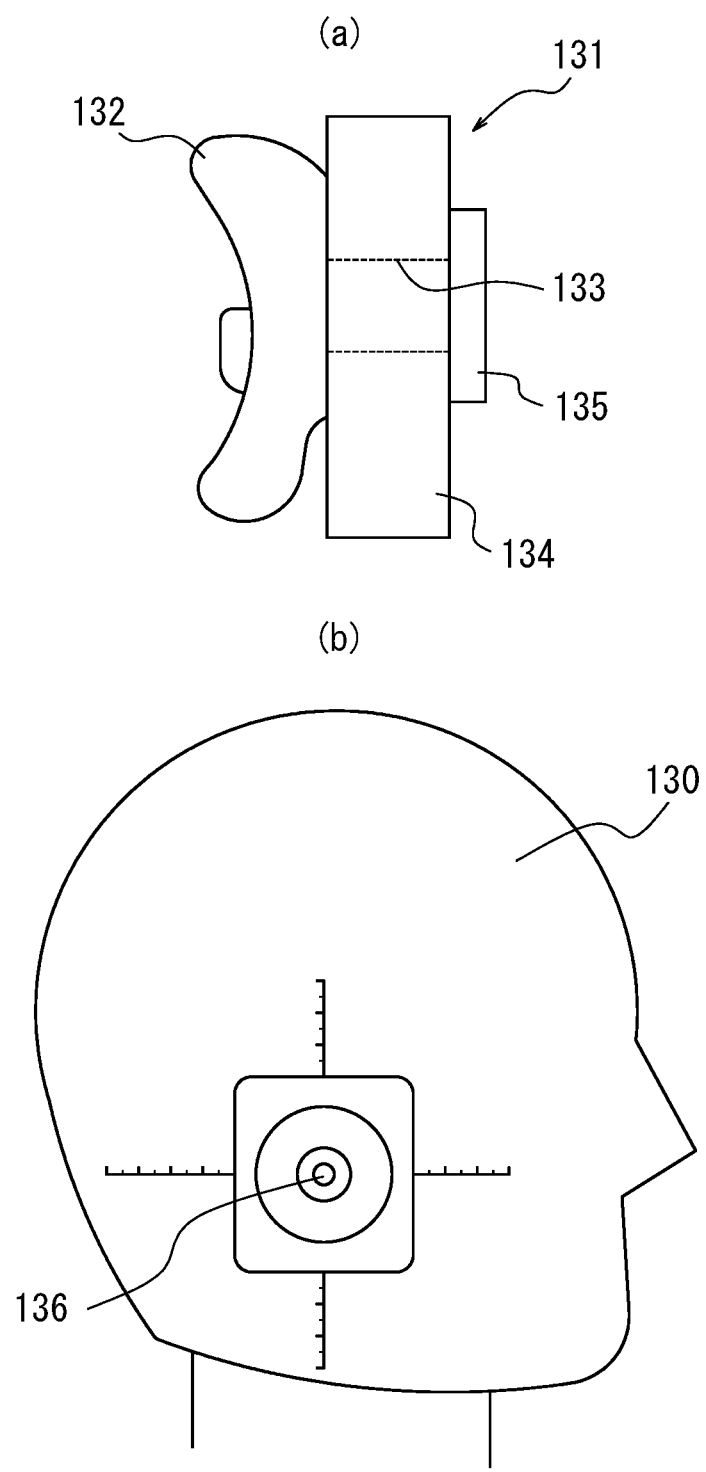
FIGS. 12A and 12B are detailed diagrams of the measurement system in FIG. 11.

The artificial ear 131 forms an ear model and includes, like the ear model 50 in Embodiment 1, an artificial auricle 132 and an artificial external ear canal unit 134, joined to the artificial auricle 132, in which an artificial external ear canal 133 is formed, as illustrated by the side view in FIG. 12A of the artificial ear 131 removed from the head model 130. Like the ear model 50 in Embodiment 1, a vibration sound gauge 55 provided with a vibration detection element is disposed at the periphery of the opening in the artificial external ear canal 133 in the artificial external ear canal unit 134. As illustrated by the side view in FIG. 12B with the artificial ear 131 removed, an air-conducted sound gauge 136 provided with a microphone is disposed in the central region on the mount for the artificial ear 131 in the head model 130. The air-conducted sound gauge 136 is disposed so as to measure sound pressure of sound propagating through the artificial external ear canal 133 of the artificial ear 131 once the artificial ear 131 is mounted on the head model 130. Like the ear model 50 in Embodiment 1, the air-conducted sound gauge 136 may be disposed on the artificial ear 131 side. The vibration detection element with which the vibration sound gauge 55 is configured and the microphone with which the air-conducted sound gauge 136 is configured are connected to the measurement unit in a similar way as in Embodiment 1.

A holder 150 is attached to the head model 130 detachably and includes a head fixing portion 151 for fixing to the head model 130, a support 152 that supports the acoustic device 1 targeted for measurement, and an articulated arm 153 connecting the head fixing portion 151 and the support 152. The holder 150 is configured so that, like the holder 70 in Embodiment 1, the pressing force and contact position, on the artificial ear 131, of the acoustic device 1 supported by the support 152 can be adjusted via the articulated arm 153.

The measurement system 110 of this embodiment yields measurement results similar to those of the measurement system 10 of Embodiment 1. Among other effects, in this embodiment, the acoustic device 1 is evaluated by detachably mounting the artificial ear 131 for vibration detection on the human head model 130, thus allowing evaluation that conforms more closely to the actual form of use by taking into consideration the effect of the head.

Although this disclosure is based on embodiments and drawings, it is to be noted that various changes and modifications will be apparent to those skilled in the art based on this disclosure. Therefore, such changes and modifications are to be understood as included within the scope of this disclosure. For example, the functions and the like included in the various units, members, and steps may be reordered in any logically consistent way. Furthermore, units and members may be combined into one or divided.

REFERENCE SIGNS LIST

1 Acoustic device (hearing aid)
10 Measurement system
10a Vibrating body
20a Microphone
20 Acoustic device mount
30 Base
31 A/D converter
32 Signal processor
33 D/A converter
34 Piezoelectric amplifier
50 Ear model
51 Artificial auricle
52 Artificial external ear canal unit
53 Artificial external ear canal
54 Support member
55 Vibration sound gauge
56 Vibration detection element
60 Air-conducted sound gauge
61 Tube member
62 Microphone
70 Holder
71 Support
72 Arm
73 Movement adjuster
110 Measurement system
120 Acoustic device mount
130 Head model
131 Artificial ear
132 Artificial auricle
133 Artificial external ear canal
134 Artificial external ear canal unit
135 Vibration detector
136 Air-conducted sound gauge
150 Holder
151 Head fixing portion
152 Support
153 Articulated arm
200 Measurement unit
300 Sensitivity adjuster
301, 302 Variable gain amplifier circuit
400 Signal processor
410 A/D converter
411, 412 A/D conversion circuit
420 Frequency characteristic adjuster
421 Equalizer
430 Phase adjuster
431 Variable delay circuit
440 Output combiner
450 Frequency analyzer
451-453 FFT
460 Memory
470 Signal processing controller
500 PC
510 Connection cable
520 Memory
530 Controller
540 Display
600 Printer

The invention claimed is:

1. A measurement system for an acoustic device including a vibrating body, wherein the acoustic device is configured to transmit sound to a user by contacting the vibrating body to a human auricle, and the acoustic device is configured to be worn by the user, the measurement system comprising: an ear model including an artificial auricle and an artificial external ear canal; and an air-conducted sound gauge configured to measure air-conducted sound in the artificial external ear canal, wherein the acoustic device is contacted to the ear model of the measurement system, the measurement system takes a measurement, with the air-conducted sound gauge, of air-conducted sound generated by the acoustic device and outputs a result of the measurement together with a characteristic of the acoustic device corresponding to when the user wears the acoustic device, and due to the vibration of the vibrating body, at least an inner wall of the artificial external ear canal vibrates, and artificial external ear canal radiated sound produced by at least the inner wall reaches and is measured by the air-conducted sound gauge.

2. A measurement system for an acoustic device including a vibrating body, wherein the acoustic device is configured to transmit sound to a user by contacting the vibrating body to a human auricle, and the acoustic device is configured to be worn by the user, the measurement system comprising: an ear model including an artificial auricle and an artificial external ear canal; and a vibration sound gauge configured to measure vibration sound in the ear model, wherein while the acoustic device is contacted to the ear model of the measurement system, the measurement system takes a measurement, with the vibration sound gauge, of vibration sound generated by the acoustic device and outputs a result of the measurement together with a characteristic of the acoustic device corresponding to when the user wears the acoustic device, wherein the vibration sound gauge is disposed annularly on an external surface of the artificial external ear canal on an opposite side from the artificial auricle.

3. A measurement system for an acoustic device including a vibrating body, wherein the acoustic device is configured to transmit sound to a user by contacting the vibrating body to a human auricle, and the acoustic device is configured to be worn by the user, the measurement system comprising: an ear model including an artificial auricle and an artificial external ear canal; an air-conducted sound gauge configured to measure air-conducted sound in the artificial external ear canal; and a vibration sound gauge configured to measure vibration sound in the ear model, wherein while the acoustic device is contacted to the ear model of the measurement system, the measurement system takes a measurement, with the air-conducted sound gauge and the vibration sound gauge, of air-conducted sound and vibration sound generated by the acoustic device and outputs combined sound, yielded by combining the air-conducted sound and the vibration sound, together with a characteristic of the acoustic device of combined sound corresponding to when the user wears the acoustic device, and due to vibration of the vibrating body, at least an inner wall of the artificial external ear canal vibrates, and artificial external ear canal radiated sound produced by at least the inner wall reaches and is measured by the air-conducted sound gauge.

4. The measurement system of claim 1, wherein the characteristic is determined with reference to predetermined data obtained by a hearing test when a predetermined air-conducted sound pressure is set as a target for an ear of the user.

5. The measurement system of claim 1, wherein the characteristic is displayed as a numerical value corresponding to a certain frequency.

6. The measurement system of claim 1, wherein the characteristic is graphically illustrated as a curve corresponding to a frequency band.

7. The measurement system of claim 1, wherein the acoustic device includes a microphone and transmits sound to the user by amplifying, with the vibrating body, sound collected with the microphone.

8. A method of adjusting an acoustic device configured to transmit sound to a user by contacting a vibrating body to a human auricle, and the acoustic device is configured to be worn by the user, the method comprising: while contacting the acoustic device, to an ear model, provided with an artificial auricle and an artificial external ear canal, of a measurement system that includes the ear model and an air-conducted sound gauge configured to measure air-conducted sound in the artificial external ear canal, displaying a predetermined result obtained by measuring, with the air-conducted sound gauge, air-conducted sound generated by the acoustic device; displaying a predetermined characteristic that corresponds to when the user wears the acoustic device; and adjusting the acoustic device based on the predetermined result and the predetermined characteristic, wherein due to vibration of the vibrating body, at least an inner wall of the artificial external ear canal vibrates, and artificial external ear canal radiated sound produced by at least the inner wall reaches and is measured by the air-conducted sound gauge.

9. A method of adjusting an acoustic device configured to transmit sound to a user by contacting a vibrating body to a human auricle, and the acoustic device is configured to be worn by the user, the method comprising: while contacting the acoustic device, to an ear model, provided with an artificial auricle and an artificial external ear canal, of a measurement system that includes the ear model and a vibration sound gauge configured to measure vibration sound in the ear model, displaying a predetermined result obtained by measuring, with the vibration sound gauge, vibration sound generated by the acoustic device; displaying a predetermined characteristic of vibration sound, the predetermined characteristic corresponding to when the user wears the acoustic device; and adjusting the acoustic device based on the predetermined result and the predetermined characteristic, wherein the vibration sound gauge is disposed annularly on an external surface of the artificial external ear canal on an opposite side from the artificial auricle.

10. A method of adjusting an acoustic device configured to transmit sound to a user by contacting a vibrating body to a human auricle, and the acoustic device is configured to be worn by the user, the method comprising: while contacting the acoustic device, to an ear model, provided with an artificial auricle and an artificial external ear canal, of a measurement system that includes the ear model, an air-conducted sound gauge configured to measure air-conducted sound in the artificial external ear canal, and a vibration sound gauge configured to measure vibration sound in the ear model, displaying predetermined combined sound that is a combination of air-conducted sound and vibration sound generated by the acoustic device and obtained by measuring, with the air-conducted sound gauge and the vibration sound gauge, the air-conducted sound and the vibration sound; displaying a predetermined characteristic of combined sound, the characteristic corresponding to when the user wears the acoustic device; and adjusting the acoustic device based on the predetermined combined sound and the predetermined characteristic, wherein due to the vibration of the vibrating body, at least an inner wall of the artificial external ear canal vibrates, and artificial external ear canal radiated sound produced by at least the inner wall reaches and is measured by the air-conducted sound gauge.

* * * * *